United States Patent
Schmidt et al.

(10) Patent No.: US 6,849,065 B2
(45) Date of Patent: Feb. 1, 2005

(54) LIQUID REMOVAL SYSTEM HAVING IMPROVED DRYNESS OF THE USER FACING SURFACE

(75) Inventors: Mattias Schmidt, Idstein (DE); Bruno Johannes Ehrnsperger, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 124 days.

(21) Appl. No.: 10/168,886

(22) PCT Filed: Dec. 20, 2000

(86) PCT No.: PCT/US00/34861
§ 371 (c)(1),
(2), (4) Date: Jun. 21, 2002

(87) PCT Pub. No.: WO01/45618
PCT Pub. Date: Jun. 28, 2001

(65) Prior Publication Data
US 2003/0004436 A1 Jan. 2, 2003

(30) Foreign Application Priority Data
Dec. 23, 1999 (EP) .......................................... 991259359

(51) Int. Cl.[7] .............................................. A61M 1/00
(52) U.S. Cl. ..................... 604/313; 604/540; 604/327; 604/355
(58) Field of Search .................... 604/313, 319–321, 604/327, 355, 540

(56) References Cited
U.S. PATENT DOCUMENTS

| 3,870,767 | A |   | 3/1975  | Grimaud et al. |
|-----------|---|---|---------|----------------|
| 4,525,166 | A | * | 6/1985  | Leclerc ........................ 604/133 |
| 4,886,508 | A | * | 12/1989 | Washington ................ 604/327 |
| 5,562,646 | A |   | 10/1996 | Goldman et al. |
| 5,599,335 | A |   | 2/1997  | Goldman et al. |
| 5,678,564 | A |   | 10/1997 | Lawrence et al. |
| 5,911,222 | A |   | 6/1999  | Lawrence et al. |
| 6,153,209 | A | * | 11/2000 | Vega et al. .................. 424/404 |
| 6,160,198 | A | * | 12/2000 | Roe et al. .................... 604/361 |
| 6,186,991 | B1 | * | 2/2001 | Roe et al. .................... 604/361 |
| 6,394,988 | B1 | * | 5/2002 | Hashimoto ................... 604/355 |
| 6,537,262 | B2 | * | 3/2003 | Thompson .................... 604/347 |
| 6,554,817 | B1 | * | 4/2003 | Oki et al. .................... 604/393 |
| 6,641,567 | B1 | * | 11/2003 | Williams .................... 604/327 |
| 6,663,610 | B1 | * | 12/2003 | Thompson et al. ......... 604/313 |
| 2002/0087131 | A1 | * | 7/2002 | Wolff et al. ................ 604/319 |

FOREIGN PATENT DOCUMENTS

| WO | WO 94/13704 A1 | 6/1994 |
|----|----------------|--------|
| WO | WO 96/00548 A1 | 1/1996 |
| WO | WO 96/16682 A1 | 6/1996 |
| WO | WO 97/42356 A1 | 11/1997 |
| WO | WO 00/00129 A1 | 1/2000 |
| WO | WO 00/00136 A1 | 1/2000 |
| WO | WO 00/00138 A1 | 1/2000 |
| WO | WO 00/00143 A2 | 1/2000 |
| WO | WO 00/00146 A2 | 1/2000 |
| WO | WO 00/14296 A1 | 3/2000 |
| WO | WO 00/14297 A1 | 3/2000 |

* cited by examiner

*Primary Examiner*—Larry I. Schwartz
*Assistant Examiner*—M. G. Bogart
(74) *Attorney, Agent, or Firm*—Edward J. Milbrada; Dara M. Kendall; Eileen L. Hughett

(57) ABSTRACT

The present invention provides a liquid removal system for applications where there is a need for liquid removal including laboratories and workshops as well as medical applications and dental applications. The urine acquisition zone of the liquid removal system of the present invention has a skin hydration value of less than 200 milligrams and hence reduces phenomena related to liquid rewet from the liquid removal system.

5 Claims, 1 Drawing Sheet

LIQUID REMOVAL SYSTEM HAVING IMPROVED DRYNESS OF THE USER FACING SURFACE

FIELD OF THE INVENTION

The present invention provides a liquid removal system for applications where there is a need for liquid removal including laboratories and workshops as well as medical applications as well as dental applications.

BACKGROUND

Articles to manage body exudates such as urine are well known in the art. In this context, managing body exudates includes acquiring, distributing, and storing body exudates such as urine, menses fecal material, and the like. A wide variety of article has been proposed including diapers, sanitary napkins, adult incontinence articles such as briefs or bed mats, underarm sweat pants, catheters, bottles, bed pans, and the like.

In U.S. Pat. No. 5,678,564 (Lawrence et al.) and U.S. Pat. No. 5,911,222 (Lawrence et al.) a liquid removal system having an interface device and a vacuum source is described. The interface device has a porous membrane with an entrance zone on one side. The vacuum source maintains a vacuum on the side of the membrane opposite the entrance zone when the membrane is wetted. Liquid which contacts the wetted porous membrane is removed from the interface device by the vacuum source. Due to its specific construction such as for example by having a exposed wetted membrane on its user facing surface, this liquid removal system not only causes a damp or wet feeling it may further lead to overhydration of the skin and finally to substantial skin problems such as irritations or infections.

Accordingly, it is an object of the present invention to provide a liquid removal system which overcomes the problems posed by the prior art.

It is a further object the present invention to provide liquid removal system which comprises a user facing surface with improved dryness during use.

SUMMARY OF THE INVENTION

The present invention provides a liquid removal system which comprises an interface device, said interface device comprising
   a first zone and
   a second zone and having
   a porous membrane separating said first zone from said second zone,
said second zone being adapted to be connected to a suction source, said porous membrane being capable of maintaining a suction in said second zone without permitting air from said first zone to pass through said membrane into said second zone when said membrane has been wetted with a first liquid; said suction being maintained until said membrane is contacted with a second liquid; and wherein said second liquid upon entering said first zone and contacting said porous membrane is removed from said first zone by said suction in said second zone by passing through said membrane into said second zone, said first zone having a user facing surface, said the second zone having a back surface, said user facing surface having a urine acquisition zone. The liquid removal system of the present invention is characterized in that the liquid removal system has a skin hydration value of less than 200 milligrams according to the collagen rewet test defined herein.

The present invention further provides a liquid removal system which comprises an interface device, said interface device comprising
   a first zone and
   a second zone and having
   a porous membrane separating said first zone from said second zone,
said second zone being adapted to be connected to a suction source, said porous membrane being capable of maintaining a suction in said second zone without permitting air from said first zone to pass through said membrane into said second zone when said membrane has been wetted with a first liquid; said suction being maintained until said membrane is contacted with a second liquid; and wherein said second liquid upon entering said first zone and contacting said porous membrane is removed from said first zone by said suction in said second zone by passing through said membrane into said second zone, said first zone having a user facing surface, said the second zone having a back surface, said user facing surface having a urine acquisition zone. The liquid removal system of the present invention is characterized in that said urine acquisition zone is completely covered by a hydrophobic apertured topsheet.

DETAILED DESCRIPTION OF THE DRAWINGS

Figure 1:
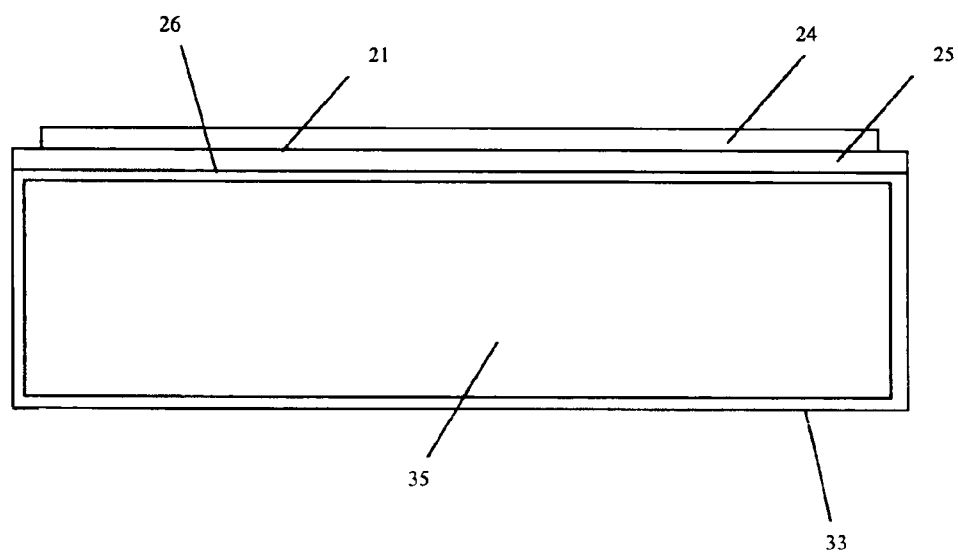
FIG. 1 shows a plan view of the absorbent article of the present invention.

FIG. 1 illustrates a liquid removal system of the present invention. The system comprises a first zone 25, a second zone 35, a user facing surface 21 of the first zone, a garment facing surface 26, and a porous membrane 33.

DETAILED DESCRIPTION OF THE INVENTION

Materials suitable for the membrane of the present invention and suction sources suitable for the liquid removal system of the present invention are described for example in U.S. Pat. No. 5,678,564 (Lawrence et al.) U.S. Pat. No. 5,911,222 (Lawrence et al.) incorporated herein by reference. Preferably, the membrane material can be bend to an extend which includes most of the typical in-use conditions without substantially loosing its functionality. More preferably, the membrane material of the present invention has a low bending moment in the longitudinal and/or the transverse direction in order to improve the comfort of the system. Preferably, the suction source as a whole or at least those parts connecting the suction source with the second zone of the liquid removal system are chosen to be flexible and/or compressible in order to improve the comfort of the system.

For the purpose of the present invention, a locally Cartesian coordinate system is defined relative to the liquid removal system and its positioning relative to the wearer during use. The longitudinal or x—direction is defined as the direction running from the front waist region of the wearer to the back waist region of the web. Typically, the longitudinal direction is the longest dimension of the liquid removal system. The transverse or y—direction is defined as direction running from the left side of the wearer to the right side of the wearer. The z—direction is normal to the x—direction and to the y—direction and accordingly is also substantially normal to the body surface of the wearer during use. It is to be understood in this context that during wear of the liquid removal system of the present invention the liquid removal system conforms to the body shape of the wearer and that accordingly the coordinate axis at the front region of the liquid removal system may not coincide with the coordinate axis in the back region of the liquid removal system.

The liquid removal system of the present invention has a user facing surface with a low rewet in order to minimize the impact of the rewet onto the skin of the wearer.

The urine acquisition zone of the liquid removal system of the present invention is completely covered by a hydrophobic apertured nonwoven topsheet. Hydrophobic apertured nonwoven web materials yield to benefits, on one hand they allow for quick penetration of acquired body liquid through the thickness dimension because of the apertures, on the other hand they do not retain liquid in their pores due to the hydrophobic nature of the fiber surface.

Topsheet

The topsheet of the present invention has a first or inner surface oriented toward the interior of the interface device of the liquid removal system, and an opposed second or outer surface oriented toward the skin of the wearer when the liquid removal system is used.

The topsheet is compliant, soft feeling, and non-irritating to the wearer's skin. Further, the topsheet is liquid pervious, permitting liquids (e.g., urine) to readily penetrate through its thickness. A suitable topsheet may be manufactured from a wide range of materials, such as porous foams; reticulated foams; apertured plastic films; or woven or nonwoven webs of natural fibbers (e.g., wood or cotton fibbers), synthetic fibbers (e.g., polyester or polypropylene fibbers), or a combination of natural and synthetic fibbers. Preferably, the topsheet is made of a hydrophobic material to isolate the wearer's skin from liquids contained in the liquid storage structure.

General Properties
Functional Properties

The topsheet of the present invention is preferably hydrophobic and in order to minimize liquid retention in the topsheet and to minimize liquid rewet from the liquid handling structure or the liquid storage structure back to the skin of the wearer.

Optionally, the topsheet of the present invention may also be oleophobic in order to minimize liquid retention in the topsheet and to minimize liquid rewet from the liquid handling structure or the liquid storage structure back to the skin of the wearer.

The topsheet of the present invention may have a liquid retention in the topsheet according to the Liquid-Retention Test defined hereinafter of less than 50 mg, preferably less than 40 mg, more preferably less than 30 mg, most preferably less than 20 mg for a test liquid having a surface tension of about 62 mN/m.

The topsheet of the present invention may have a liquid retention in the topsheet according to the Liquid-Retention Test defined hereinafter of less than 150 mg, preferably less than 120 mg, more preferably less than 90 mg, most preferably less than 70 mg for a test liquid having a surface tension of about 33 mN/m.

The contact angle of the user facing side of the topsheet of the present invention with distilled water having a surface tension of at least 72 mN/m may be at least 90°, preferably at least 100°, more preferably at least 110°, even more preferably at least 120°, most preferably more than 125°. High contact angles reduce the capillary suction of the pores of the topsheet. Contact angles of more than 90° even result in a negative the capillary suction, hence rendering the respective pores water repellent.

Structural Properties

The topsheet preferably has a plurality of apertures with an effective aperture size of at least 0.2 square millimeters, more preferably, the plurality of apertures have an effective aperture size of at least 0.5 square millimeters, even more preferably, the plurality of apertures have an effective aperture size of at least 1.0 square millimeters, and most preferably, the plurality of apertures have an effective aperture size of at least 2.0 square millimeters. Effective apertures are those which have a gray level of 18 or less on a standard gray level scale of 0–255, under the image acquisition parameters described below.

The topsheet preferably can have an effective open area of at least 15 percent, more preferably the topsheet has an effective open area of at least 20 percent, even more preferably, the topsheet has an effective open area of at least 25 percent, and most preferably the topsheet has an effective open area of at least 30 percent.

A method to determine effective aperture size and open area is described in the method section.

Manufacturing Techniques

Suitable materials and structures for use as the topsheet may include apertured nonwoven webs, apertured films, apertured formed films, scrims, woven webs, scrim, netting, macroporous thin foams, composites of the aforementioned materials, and the like. There are a number of manufacturing techniques which may be used to manufacture the topsheet 24. For example, the topsheet may be a nonwoven web of fibbers spunbonded, carded, wet-laid, meltblown, hydroentangled, combinations or composite laminates of the above, or the like. Preferred topsheets include a carded/carded composite, hydroentangled over a wire forming screen and thermally air-through bonded by means well known to those skilled in the nonwovens art and hydroentanglement of fibrous webs.

Surface Treatment

The topsheet of the absorbent article of the present invention may comprises a surface finish to increase the surface energy of the topsheet to at least 40 mN/m, preferably at least 45 mN/m, more preferably 50 mN/m, most preferably at least 60 mN/m. Suitable surfactants and suitable manufacturing techniques are well known in the art.

The topsheet of the present invention may also comprise a surface finish reducing the surface free energy of at least a part of the surface of the topsheet and hence rendering this part of the surface even more hydrophobic and eventually oleophobic.

The structured may comprise hydrophobicity gradients in a direction parallel to the major surfaces of the topsheet to provide individual liquid handling properties in different regions of the topsheet. The topsheet may also comprise a hydrophobicity gradient in a direction perpendicular to the major surfaces of the topsheet in order to enhance liquid transfer through the topsheet.

At least a part of the surface, and in particular of the surface facing the wearer during use, of the topsheet may comprise a surface coating such as a thin fluorocarbon polymer film. Suitable techniques to obtain such a surface coating are well known in the art and are described for example in European patent application No. 98116895.8, in WO 97/42356 (Gleason) and in WO96/00548 (Ouellette). Another suitable surface treatment is a silicone release coating from Dow Corning of Midland, Mich. available as Syl-Off 7677 to which a cross-linker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-DI, in proportions by weight of 100 parts to 2.5 parts, respectively. Another suitable treatments include fiber finishs available from Fibervisions of Varde, Denmark, under the designations T190 and T198, a fiber finish available from Schill and Seilacher of Böblingen, Germany, under the designation Silastol FC1760, a melt-in additive available from the Minnesota Mining And Manufacturing Company, of St. Paul, Minn., USA. Other suitable treatment materials include, but are not limited to, fluorinated materials such as fluoropolymers (e.g., polytetrafluoroethylene (PTFE), commercially available under the trade name TEFLON) and chlorofluoropolymers. Other materials which may prove suitable for providing regions of reduced surface energy include Petrolatum, latexes, paraffins, and the like.

The topsheet of the present invention may comprise hydrophobic and oleophobic polymers. Processes to manufacture such polymers and articles therefrom is well known in the art and are described for example in U.S. Pat. No. 3,870,767 (Grimaud).

Optionally, the topsheet of the present invention may be treated by modulated plasma glow discharge treatments as described in European patent application No. 98116895.8 (D'Agostino et al., P&G case CM 1893FQ) and European patent application No. 98116894.1 (D'Agostino, P&G case CM 1894FQ).

Skin Care Composition

The outer surface of the topsheet may comprise an effective amount of a skin care composition which is semi-solid or solid at 20° C. and which is partially transferable to the wearer's skin. In preferred embodiment of the absorbent article of the present invention, the absorbent article additionally comprises an skin care composition which is at least partially transferable to the skin of the user during the intended use. Preferably, such an oil-containing composition is positioned on a user facing surface of the absorbent article. The oil-containing composition may also be deployed in such a way that it is only released at the time of intended use such as being microencapsulated.

Skin care compositions suitable for the absorbent article of the present invention are described for example in WO96/16682 (Roe et al.).

Preferably, the skin care compositions suitable for the absorbent article of the present invention have a melting profile such that they are relatively immobile and localized regarding their positioning within the absorbent article at room temperature, are transferable to the user at body temperature, and yet are not completely liquid under extreme storage conditions. Importantly, the skin care compositions of the present invention are easily transferable to the skin by way of normal contact, user motion, and/or body heat.

The skin care compositions suitable for the absorbent article of the present invention are solid, or more often semisolid, at 20° C., i.e. at ambient temperatures. By "semi-solid" it is meant that the skin care composition has a rheology typical of pseudoplastic or plastic fluids. When no shear is applied, the skin care compositions can have the appearance of a semi-solid but can be made to flow as the shear rate is increased. This is due to the fact that, while the skin care composition contains primarily solid components, it also includes some minor liquid components.

The skin care compositions suitable for the absorbent article of the present invention are at least semi-solid at room temperature to minimize skin care composition migration. In addition, the skin care compositions preferably have a final melting point (100% liquid) above potential "stressful" storage conditions that can be greater than 45° C.

Specifically, the skin care compositions suitable for the absorbent article of the present invention should have the following melt profile:

| Characteristic | Preferred Range | Most Preferred |
| --- | --- | --- |
| % liquid at room temp (20° C.) | 2–50 | 3–25 |
| % liquid at body temp. (37° C.) | 25–95 | 30–90 |
| final melting point (° C.) | >=38 | >=45 |

By being solid or semisolid at ambient temperatures, these skin care compositions do not have a tendency to flow and migrate into the interior of the absorbent article to which they are applied. This means less skin care composition is required for imparting desirable therapeutic or protective coating benefits.

When applied to the user facing surface of absorbent article of the present invention, the skin care compositions suitable for the absorbent article of the present invention are transferable to the user's skin by normal contact, user motion, and/or body heat.

A preferred embodiment of the absorbent article of the present invention contains an effective amount of an skin care composition. As used herein, the term "effective amount of an skin care composition coating" refers to an amount of a particular skin care composition which, when applied to a diaper topsheet, will be effective in fulfilling their protective, therapeutic, or cosmetic intention. Of course, the effective amount of a skin care composition coating will depend, to a large extent, on the particular skin care composition used.

The skin care compositions suitable for the absorbent article of the present invention comprise: (1) an emollient(s); (2) an immobilizing agent(s) for the emollient; (3) optionally a hydrophilic surfactant(s); and (4) other optional components.

The viscosity of the formulated skin care compositions, including emollient, immobilizing agent, and optional components should be as high as possible to keep the skin care composition from flowing into the interior of the absorbent article. Unfortunately, high viscosities can also lead to skin care compositions that are difficult to apply without processing problems. Therefore, a balance must be achieved so the viscosities are high enough to keep the skin care compositions localized on the user facing surface of the absorbent article, but not so high as to cause processing problems. Suitable viscosities for the skin care compositions will typically range from about 5 to about 200 centipoises, preferably from about 15 to about 100 centipoises, measured at 60° C.

Emollient

The key active ingredient in these skin care compositions is one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. For being suitable to be used in the absorbent article of the present invention, these emollients have either a plastic or fluid consistency at i.e., at ambient temperatures. This particular emollient consistency allows the skin care composition to impart a soft, lubricious, lotion-like feel.

Emollients useful in the absorbent article of the present invention can be petroleum-based, fatty acid ester type, alkyl ethoxylate type, fatty acid ester ethoxylates, fatty alcohol type, polysiloxane type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for skin care compositions of the present invention.

Immobilizing Agent(s) for the Emollient

The immobilizing agent counteracts the tendency of the emollient to migrate or flow into the absorbent article of the present invention by keeping the emollient primarily localized on the surface of the absorbent article to which the skin care composition is applied.

Suitable immobilizing agents for the use in the absorbent article of the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear.

Optional Hydrophilic Surfactant(s)

It is important that the skin care composition also be sufficiently wettable to ensure that liquids can rapidly penetrate into at least the first component of the absorbent article. This diminishes the likelihood that body exudates will flow off the skin care composition coating rather than being drawn into at least the first component. Depending upon the particular immobilizing agent used in the skin care composition of the present invention, an additional hydrophilic surfactant (or a mixture of hydrophilic surfactants) may, or may not, be required to improve wettability.

Other Optional Components

Oil-based compositions can comprise other optional components typically present in emollient, creams, and skin care compositions of this type. These optional components include water, viscosity modifiers, perfumes, disinfectant antibacterial actives, pharmaceutical actives, film formers, deodorants, opacifiers, astringents, solvents and the like. In addition, stabilizers can be added to enhance the shelf life of the skin care composition such as cellulose derivatives, proteins and lecithin. All of these materials are well known in the art as additives for such formulations and can be employed in appropriate amounts in the skin care compositions of the present invention.

As is readily apparent to the skilled person, the reduction of surface wetness can only be achieved by providing a liquid removal system exhibiting a sufficient performance for example in terms of acquisition rate, liquid transportation rate, storage capacity, membrane performance, and the like.

In the following, a suitable embodiment of the liquid removal system and of suitable members for a liquid removal system respectively will be described. The liquid removal system is assembled from an open celled foam material which is completely enveloped by a membrane. A suitable membrane material is available from SEFAR of Rüschlikon, Switzerland, under the designation SEFAR 03-20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid removal system, it may also be required to choose similar materials with slightly different properties. After assembly, the liquid removal system is activated by immersing the liquid removal system in water or in synthetic urine until the liquid removal system is completely filled with liquid and until the membranes are completely wetted with liquid. After activation, a part of the liquid inside the liquid removal system may be squeezed out by applying an external pressure to the liquid removal system. If the activation of the liquid removal system was successful, the liquid removal system should not suck air through the membranes.

The particular geometry of the liquid removal system of the present invention can be varied to according to the specific requirements off the intended application. If, for example, the liquid removal system is intended to be used in an absorbent article the liquid removal system may be defined such that its zone of intended liquid acquisition fits between the legs of the wearer and further that its intended liquid discharge zone matches the form of the storage member associated to it. Accordingly, the outer dimensions of the liquid removal system such as length, width, or thickness may also be adapted to the specific needs of the intended application. In this context, it has to be understood, however, that the design of the outer form of the liquid removal system may have an impact on its performance. For example, the cross section of the liquid removal system directly impacts on its flow rate.

For application of the liquid removal system in an absorbent article according to the present invention, the liquid removal system is combined with a storage member. The term "liquid storage member" refers to an article which is capable of acquiring and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. In order to pick up the liquid discharged from the liquid removal system, the storage member may be placed in direct liquid communication with the intended liquid discharge zone of the liquid removal system. A suitable storage member is for example a superabsorbent polymer such as available from CHEMDAL, United Kingdom, under the designation ASAP400.

Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

Other liquid removal systems suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications PCT/US99/14796 entitled "High flux liquid transport members comprising two different permeability regions" (P&G case CM1840MQ) filed in the name of Ehrnsperger et al., PCT/US99/14654 entitled "Liquid transport member for high flux rates between two port regions" (P&G case CM1841 MQ) filed in the name of Ehrnsperger et al., PCT/US99/14638 entitled "Liquid transport member for high flux rates against gravity" (P&G case CM1842MQ) filed in the name of Ehrnsperger et al., PCT/US99/14633 entitled "Liquid transport member having high permeability bulk regions and high bubble point pressure port regions" (P&G case CM1843MQ) filed in the name of Ehrnsperger et al. All of these documents are enclosed herein by reference.

In one embodiment of the present invention, the liquid removal system of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules a according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases a solid material and a gas or void phase—and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

In one embodiment of the present invention, the absorbent article is a disposable absorbent article such as a diaper, a training pant, a sanitary napkin, an adult incontinence article, or the like. Such an absorbent article may further comprise a liquid pervious topsheet, a liquid impervious backsheet at least partially peripherally joined to the topsheet. The absorbent article may further comprise an absorbent core which may serve as a storage member for the urine. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

Methods

Unless stated otherwise, all tests are carried out at about 22° C.+/−2° C. and at 35+/−15% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of(NH4)H2PO4; 0.15 g/l (NH4)2HPO4; 0.19 g/l of CaCl2; ad 0.23 g/l of MgCl2. All of the chemicals are of reagent grade. The pH of the synthetic Urine is in the range of 6.0 to 6.4.

Finished-Product-Acquisition Test

An liquid removal structure is loaded with a 75 ml gush of synthetic urine at a rate of 15 ml/s using a pump (Model 7520-00, supplied by Cole Parmer Instruments., Chicago, USA), from a height of 5 cm above the sample surface. The time to absorb the urine is recorded by a timer. The gush is repeated every 5 minutes at precisely 5 minute gush intervals until the article is sufficiently loaded. Current test data are generated by loading four times.

The test sample, which at least includes the interface device of the liquid removal system, is arranged to lie flat on a foam platform within a perspex box. In this context, the term "flat" refers to the urine acquisition zone of the liquid removal system. A perspex plate having a 5 cm diameter opening substantially in its middle is placed on top of the urin acquisition zone of the sample. Synthetic urine is introduced to the sample through a cylinder fitted, and glued into the opening. Electrodes are located on the lowest surface of the plate, in contact with the surface of the absorbent structure. The electrodes are connected to the timer. Loads are placed on top of the plate to simulate, for example a baby's weight. A pressure of 50g cm2 (0.7 psi) is typically utilized in this test.

As test fluid is introduced into the cylinder it typically builds up on top of the liquid removal system thereby completing an electrical circuit between the electrodes. This starts the timer. The timer is stopped when the absorbent structure has absorbed the gush of urine, and the electrical contact between the electrodes is broken. In case, test fluid does not build up in the cylinder, the absorption time is set to be zero.

The acquisition rate is defined as the gush volume absorbed (ml) per unit time (s). The acquisition rate is calculated for each gush introduced into the sample. Of particular interest in view of the current invention are the first and the last of the four gushes.

This test is primarily designed to evaluate systems having an absorbent capacity of about 300 ml to 400 ml. If products with significantly different capacities should be evaluated, the settings in particular of the fluid volume per gush should be adjusted appropriately to about 20% of the theoretical capacity, and the deviations should be recorded.

Liquid Retention Test

The liquid retention test measures the liquid that is retained in a material sample that is temporarily immersed in a test liquid having defined surface tension. The test liquids are prepared by using distilled water and dissolving a suitable amount of suitable surfactant in the water.

A sample of the material having dimension of 50 mm length and 50 mm width is prepared and weighed. The sample is immersed in the test liquid for about 5 minutes. After taking the sample out of the test liquid, the sample is carefully shaken so that excess liquid can run off from the surface of the material sample.

The liquid retention of the material sample is obtained by measuring the wet weight and taking the difference between wet weight and dry weight.

Collagen Rewet Test Method

Before executing the test, the collagen film as purchased from NATURIN GmbH, Weinheim, Germany, is prepared by being cut into circular sheets of 90 mm diameter by using a sample cutter device and by equilibrating the film in the controlled environment of the test room (see above) for at least 12 hours (tweezers are to be used for all handling of the collagen film).

At least 5 minutes, but not more than 6 minutes after the last gush of the above acquisition test is absorbed, the cover plate and weights are removed, and the test sample is carefully placed flat on a lab bench.

4 sheets of the pre-cut and equilibrated collagen material are weighed with at least one milligram accuracy, and then positioned centered onto the loading point of the liquid removal system, and covered by perspex plate of 90 mm diameter, and about 20 mm thickness. A weight of 15 kg is carefully added (also centered). After 30+/−2 seconds the weight and perspex plate are carefully removed again, and the collagen films are reweighed.

The Skin Hydration Value is the moisture pick up of the collagen film, expressed in milligrams.

What is claimed is:

1. An absorbent article comprising a liquid removal system and a storage member, said liquid removal system which comprises an interface device, said interface device comprising a first zone and a second zone and having a porous membrane separating said first zone from said second zone, said second zone being activated to provide a lower pressure therein than said first zone so as to provide a suction, said porous membrane being capable of maintaining a suction in said second zone without permitting air from said first zone to pass through said membrane into said second zone when said membrane has been wetted with a first liquid; said suction being maintained until said membrane is contacted with a second liquid; and wherein said second liquid upon entering said first zone and contacting said porous membrane is removed from said first zone by said suction in said second zone by passing through said membrane into said second zone said first zone having a user facing surface, said second zone having a back surface, said user facing surface having a urine acquisition zone, said second zone being in liquid communication with said storage member wherein said storage member imbibes liquid from said liquid removal system by at least one of capillary suction and osmotic pressure, said storage member comprising a superabsorbent polymer, characterized in that said liquid removal system has a skin hydration value of less than 200 milligrams.

2. A liquid removal system according to claim 1 wherein said user facing surface comprises a skin care composition which is at least partially transferable to the skin of the user during use of said liquid removal system.

3. A liquid removal system which comprises an interface device and a storaae member, said interface device comprising a first zone and a second zone and having a porous membrane separating said first zone from said second zone, said second zone being activated to provide a lower pressure than said first zone so as to provide a suction, said porous membrane being capable of maintaining a suction in said second zone without permitting air from said first zone to pass through said membrane into said second zone when said membrane has been wetted with a first liquid; said suction being maintained until said membrane is contacted with a second liquid; and wherein said second liquid upon entering said first zone and contacting said porous membrane is removed from said first zone by said suction in said second zone by passing through said membrane into said second zone said first zone having a user facing surface, said second zone having a back surface, said user facing surface having a urine acquisition zone characterized in that said urine acquisition zone is completely covered by a hydrophobic apertured topsheet, said second zone being in liquid communication with said storage member wherein said storage member imbibes liqiuid from said liquid removal system by at least one of capillary suction and osmotic pressure, said storage member comprising a superabsorbent polymer.

4. A liquid removal system according to claim 3 wherein the user facing surface of said hydrophobic apertured nonwoven topsheet comprises a skin care composition which is at least partially transferable to the skin of the user during use of said liquid removal system.

5. A liquid removal system according to claim 3 wherein set hydrophobic apertured nonwoven topsheet has a liquid retention of less than 50 mg for a test liquid having a surface tension of about 62 mN/m.

* * * * *

UNITED STATES PATENT AND TRADEMARK OFFICE
CERTIFICATE OF CORRECTION

PATENT NO. : 6,849,065 B2
DATED : February 1, 2005
INVENTOR(S) : Mattias Schmidt et al.

It is certified that error appears in the above-identified patent and that said Letters Patent is hereby corrected as shown below:

Column 5,
Line 6, delete "UV 9380C-DI," and insert -- UV 9380C-D1, --.
Line 29, delete "CM 1893FQ)" and insert -- CM1893FQ) --.
Line 31, delete "CM 1894FQ)." and insert -- CM1894FQ). --.

Column 9,
Line 22, delete "CM1841 MQ)" and insert -- CM1841MQ) --.

Column 10,
Line 32, delete "2.0 g/:" and insert -- 2.0 g/l --.
Line 33, delete "Na2SO4:" and insert -- $Na_2SO_4$; --.
Line 33, delete "(NH4)H2PO4;" and insert -- "$(NH_4)H_2PO_4$; --.
Line 34, delete "(NH4)2HPO4;" and insert -- "$(NH_4)H_2PO_4$; --.
Line 34, delete "CaC12;" and insert -- $CaCl_2$; --.
Line 34, delete "ad 0.23 g/l of MgCl2." and insert -- and 0.23 g/1 of $MgCl_2$. --.
Line 36, delete "Urine" and insert -- urine --.
Line 58, delete "50g cm2" and insert -- 50 g $cm^{-2}$ --.

Column 12,
Line 23, delete "storaae" and insert -- storage --.
Line 43, delete "liqiuid" and insert -- liquid --.

Signed and Sealed this

Twenty-eighth Day of February, 2006

JON W. DUDAS
*Director of the United States Patent and Trademark Office*